(12) United States Patent
Kaizawa et al.

(10) Patent No.: US 6,316,780 B1
(45) Date of Patent: Nov. 13, 2001

(54) BODY ATTITUDE SCREENING APPARATUS FOR SLIDE FASTENER SLIDER

(75) Inventors: Syuuichi Kaizawa; Wataru Matsushima, both of Toyama-ken (JP)

(73) Assignee: YKK Corporation, Tokyo (JP)

( * ) Notice: Subject to any disclaimer, the term of this patent is extended or adjusted under 35 U.S.C. 154(b) by 0 days.

(21) Appl. No.: 09/363,735

(22) Filed: Jul. 30, 1999

(30) Foreign Application Priority Data

Aug. 7, 1998 (JP) ................................................. 10-224204

(51) Int. Cl.$^7$ ................................................. G01N 21/86
(52) U.S. Cl. ................................................. 250/559.4
(58) Field of Search ........................... 250/559.4, 559.43, 250/206, 206.2, 559.29, 559.12, 559.01

(56) References Cited

U.S. PATENT DOCUMENTS 5,065,898 * 11/1991 Michalewski et al. .............. 221/171
5,201,205 * 4/1993 Zieve et al. ................................. 72/31
5,823,356 * 10/1998 Goodrich et al. .................... 209/601

* cited by examiner

Primary Examiner—Frank G. Font
Assistant Examiner—Michael P. Stafira
(74) Attorney, Agent, or Firm—Finnegan, Henderson, Farabow, Garrett & Dunner, L.L.P.

(57) ABSTRACT

The present invention provides a body attitude screening apparatus for a slide fastener slider, with which it is unnecessary to adjust the apparatus to be adapted to respective bodies in different shapes of the slide fastener slider, sharing of the same apparatus for screenings of the bodies in the different shapes is possible, and the screening of the bodies based on their attitudes is easy. The body attitude screening apparatus of the slide fastener slider for supplying the body of the slide fastener slider includes a transferring passage on which the bodies move and a sensing portion which is provided to some midpoint of the transferring passage and which detects an attitude of each the body. The sensing portion has a presence/absence distinguishing sensor for sensing the body and an attitude distinguishing sensor for distinguishing the attitude of the body. The attitude distinguishing sensor has light emitting portions and light receiving portions. End portions of optical fibers for constituting the attitude distinguishing sensor and guiding light are positioned on the transferring passage.

5 Claims, 2 Drawing Sheets

BODY ATTITUDE SCREENING APPARATUS FOR SLIDE FASTENER SLIDER

BACKGROUND OF THE INVENTION

1. Field of the Invention

The present invention relates to a body attitude screening apparatus for a slide fastener slider used when a body of the slide fastener slider is supplied to an assembling device and the like.

2. Description of the Related Art

Conventionally, a guiding method has been mainly employed for a general body attitude screening apparatus of a slide fastener slider. In the guiding method, a plurality of parts in a bowl of the body attitude screening apparatus receive torsional vibrations so as to be fed onto a transferring passage and are screened based on their attitudes in a screening portion provided at a predetermined position of the apparatus, and only the parts in a desired attitude are supplied in sequence. The parts in other attitudes are dropped in the screening portion and returned into the bowl of the body attitude screening apparatus again.

In the guiding method, in many cases, the special transferring passage corresponding to a shape of the parts is used. For attitude screening of parts in different shapes, it has been necessary to adjust the transferring passage and the screening portion to be suitable for the shapes of the respective parts.

There is proposed an attitude screening apparatus as disclosed in Japanese Patent Publication No. 60-14739, wherein electrically detecting means and eliminating means are provided to the screening portion to mechanically eliminate parts in attitudes other than a desired attitude.

In the case of the former prior art, a special transferring passage corresponding to a shape of each slider body is necessary in the body attitude screening apparatus, and sharing of the same body attitude screening apparatus for screening the attitude of the bodies in different shapes is impossible. Changing of the transferring passage and the screening portion for each kind of body requires experience and a large number of steps of operation.

When the latter prior art apparatus is used for supplying the body of the slide fastener slider, a shape of the body of the slide fastener slider is peculiar and intricate and it is extremely difficult to electrically and optically sense the attitude of the body based on an outside shape of the body. Furthermore, when a technique such as a pattern recognition is used, a structure of a sensing portion becomes intricate.

SUMMARY OF THE INVENTION

The present invention has been developed with the above-described problems of prior art in view, and it is an object of the invention to provide a body attitude screening apparatus for a slide fastener slider, wherein it is unnecessary to adjust the apparatus to be adapted to each body, sharing of the same apparatus for screenings of the bodies in the different shapes is possible, and switching for adapting the apparatus to different kinds of bodies is easy.

To achieve the above objects, according to the invention, there is provided a body attitude screening apparatus for a slide fastener slider for transferring bodies along a transferring passage, sensing attitudes of the bodies, and supplying only the bodies in a desired attitude. Each of the bodies has a flat upper and lower plates disposed in parallel to each other, a connecting post connecting the upper and lower plates, and a tape groove defined between the upper and lower plates. The apparatus comprises a sensing portion which is provided at the transferring passage on which the bodies are transferred and which electrically senses the attitudes of the bodies. And the sensing portion has a presence/absence distinguishing sensor for distinguishing presence and absence of each the body and an attitude distinguishing sensor for distinguishing the attitude of each the body in a direction orthogonal to a traveling direction of the body based on sensing of the presence/absence distinguishing sensor.

The attitude distinguishing sensor has two pairs of adjacent light emitting portions and light receiving portions and the attitude distinguishing sensor is disposed to distinguish the attitudes of the bodies based on two states, i.e., a state in which one of lights passing between the two pairs of light emitting portions and light receiving portions passes through the tape groove of each the body moving on the transferring passage and a state in which both the lights are intercepted by the connecting post of the body moving on the transferring passage. The transferring passage has a transferring face inclined in a direction orthogonal to the traveling direction of the bodies and a guide portion connected to the transferring face along a lower end of the transferring face and projecting perpendicularly to the transferring face, any ones of the light emitting portions and the light receiving portions are disposed in the guide portion, and the others are disposed at a distance from the ones of the light emitting portions and the light receiving portions to face the ones of the light emitting portions and the light receiving portions.

The light emitting portions and the light receiving portions are disposed at diagonal positions displaced forward and backward from each other with respect to the traveling direction of the bodies. In addition, the presence/absence distinguishing sensor has a light emitting portion and a light receiving portion disposed at positions on front and rear face sides of the transferring passage to face each other with the transferring passage disposed therebetween.

DESCRIPTION OF THE PREFERRED EMBODIMENT

Figure 1:
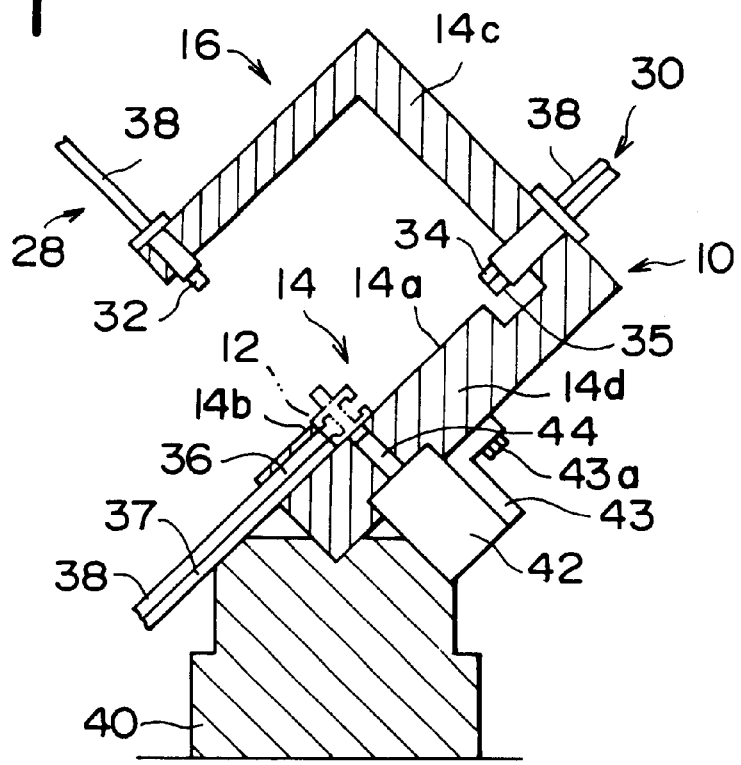
FIG. 1 is a cross sectional view of a sensing portion of a body attitude screening apparatus according to an embodiment of the present invention.
Figure 2:
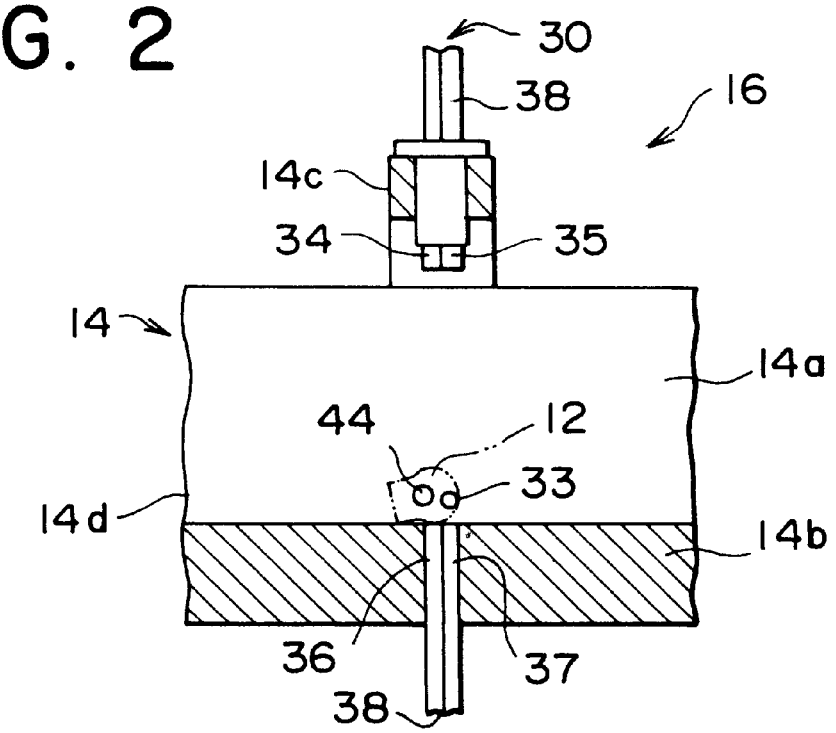
FIG. 2 is a longitudinal sectional view of the sensing portion of the body attitude screening apparatus of the embodiment of the invention.

An embodiment of the present invention will be described below based on the drawings. FIGS. 1 and 2 show a body attitude screening apparatus 10 for a slide fastener slider of the embodiment of the invention and a sensing portion 16 which is for attitude screening a body 12 as an object to be screened of the slide fastener slider and which is provided at some midpoint of a transferring passage 14. The transferring passage 14 comprises a transferring face 14a inclined in such a direction to be perpendicular to a traveling direction of the bodies 12, i.e., in such a direction to cross the traveling direction and a guide portion 14b connected to the transferring face 14a along a lower end of the transferring face 14a and projecting perpendicularly to the transferring face 14a and the transferring passage 14 is substantially in an L shape in section in the direction perpendicular to the traveling direction. As shown in FIG. 1, the transferring passage 14 is inclined 45° with respect to a horizontal plane and carries the body 12 in an inclined attitude with a lower plate 22 of the body 12 which will be described later being in contact with the transferring face 14a and one side edge portions and guide flanges 20a and 22a on the same side of an upper plate 20 and the lower plate 22 of the body 12 being in contact with the guide portion 14b.

Figure 3A:
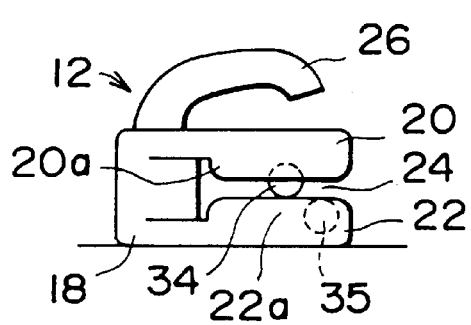
FIG. 3A is a right side view of the body to be screened in the body attitude screening apparatus of the embodiment of the invention.
Figure 3B:
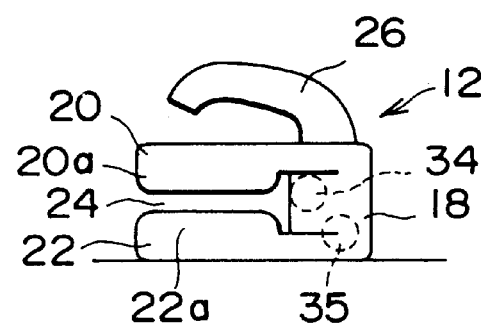
FIG. 3B is a left side view of the body to be screened in the body attitude screening apparatus of the embodiment of the invention.

The body 12 comprises the flat upper and lower plates 20 and 22 which are disposed in parallel to each other and a connecting post 18 connecting front ends of the upper and lower plates 20 and 22 as shown in FIGS. 3A and 3B. The respective upper and lower plates 20 and 22 have at side edge portions thereof the guide flanges 20a and 22a standing perpendicularly to face each other. A tape groove 24 is defined between the respective guide flanges 20a and 22a. A pull tab attaching post 26 is provided on an upper portion of the connecting post 18 so as to stand from the upper plate 20 and extend from a front end side toward a rear end side of the body 12. Such a body 12 of the slider is, applied to a slide fastener chain wherein coupling elements made of metal are attached to core portions continuously formed along opposed side edge portions of a pair of fastener tapes such that the coupling elements are symmetrically disposed on a front surface and a rear faces of each fastener tape, for example.

The sensing portion 16 of the body attitude screening apparatus 10 for the slide fastener slider of the present embodiment comprises a presence/absence distinguishing sensor 28 for sensing that the body 12 of the slide fastener slider has reached a predetermined position and an, attitude distinguishing sensor 30 for sensing an attitude of the body 12. The presence/absence distinguishing sensor 28 has a light emitting portion 32 and a light receiving portion 33 facing each other with the transferring passage 14 disposed therebetween. The light emitting portion 32 is disposed substantially right above the body 12 which moves on the transferring passage 14. A base end of the light emitting portion 32 is fixed to a tip end of an L-shaped frame 14c extending from the transferring passage 14. The light receiving portion 33 is disposed in the transferring face 14a of a substrate 14d constituting the transferring passage 14 to be substantially perpendicular to the transferring passage 14 and to face the light emitting portion 32.

On the other hand, the attitude distinguishing sensor 30 has two pairs of light emitting portions 34 and 35 and light receiving portions 36 and 37. The attitude distinguishing sensor 30 is disposed at such a position that the presence/absence distinguishing sensor 28 and the attitude distinguishing sensor 30 are orthogonal to each other at the body 12 moving on the transferring passage 14. The light emitting portions 34 and 35 are disposed in parallel to the transferring face 14a of the transferring passage 14. The light emitting portions 34 and 35 are disposed to irradiate predetermined positions of the guide flanges 20a and 22a and the tape groove 24 of the body 12 on the transferring passage 14. The light receiving portions 36 and 37 are disposed at such positions in the transferring passage 14 as to face the light emitting portions 34 and 35. Optical fibers 38 are positioned at tip end portions of the respective light emitting portions 32, 34, and 35 and light receiving portions 33, 36, and 37 of the presence/absence distinguishing sensor 28 and the attitude distinguishing sensor 30, and light is guided from light sources through the optical fibers 38, received by the optical fibers 38 at the light receiving portions, and guided to light receiving elements (not shown).

In the body attitude screening apparatus 10, an air cylinder 42 is fixed to a substrate 14d of the transferring passage 14 through a fixing plate 43 by a bolt 43a, the air cylinder 42 being adjacent to the light receiving portion 33 of the presence/absence distinguishing sensor 28. The air cylinder has an eject pin 44 and a thrusting operation of the eject pin 44 is carried out by a driving device (not shown).

In the body attitude screening apparatus 10 for the slide fastener slider of the embodiment, in order to screen the bodies 12 based on their attitudes, the large number of bodies 12 accommodated in the bowl (not shown) of the body attitude screening apparatus 10 are let off onto the transferring passage 14 in sequence as they receive torsional vibrations from a vibrating body 40. When each the body 12 reaches a position where the presence/absence distinguishing sensor 28 is provided, the body 12 intercepts the light between the light emitting portion 32 and the light receiving portion 33. As a result, the presence/absence distinguishing sensor 28 transmits a signal for indicating that the body 12 has reached a predetermined position, in response to which the attitude distinguishing sensor 30 is actuated to distinguish a received state of the lights emitted from the light emitting portions 34 and 35 toward the connecting post 18, the guide flanges 22a of the lower plate 22, and the tape groove 24 of the body 12.

The transferring passage 14 may be in any form such as a curved passage formed on an inner face of the bowl or a straight passage formed on a surface of the flat substrate 14d.

Assuming that the body 12 shown in FIG. 3A is in a desired attitude, i.e., an attitude wherein the connecting post 18 is on a rear side in the traveling direction of the body 12 and that the body 12 is traveling rightward in FIG. 3A, the light emitted from the light emitting portion 35 of the attitude distinguishing sensor 30 is intercepted by the guide flange 22a of the lower plate 22 of the body 12 and does not reach the light receiving portion 37. On the other hand, the light emitted from the light emitting portion 34 of the attitude distinguishing sensor 30 passes through the tape groove 24 and reaches the light receiving portion 36.

However, when the body 12 is in a reverse orientation as shown in FIG. 3B, namely, when the connecting post 18 is positioned on a front side in the traveling direction of the body 12, the lights emitted from both the light emitting portions 34 and 35 are intercepted by the connecting post 18 of the body 12 and does not reach the light receiving portions 36 and 37. In this case, it is sensed that the body 12 is in the attitude different from the desired attitude. Then, the cylinder 42 is actuated and the eject pin 44 of the air cylinder 42 thrusts from a surface of the transferring face 14a to push out the body 12 in the different attitude and to return the body 12 into the bowl. The bodies 12 in the desired attitude are transferred in the traveling direction and supplied to a next station one by one.

When the same body attitude screening apparatus 10 for the slide fastener slider is used and the attitude of the body 12 shown in FIG. 3B is a desired attitude and the bodies 12 in the desired attitude are to be sorted out, it is possible to previously program the apparatus to distinguish the one with which the lights emitted from both the light emitting portions 34 and 35 of the attitude distinguishing sensor 30 are intercepted by the connecting post 18 is taken as a proper case and it is easily realized to switch between the cases of different attitudes by a switch and the like. At this time, it is unnecessary to change the transferring passage 14 and the bowl or to change positions and orientations of the respective sensors 28, 30.

Figure 4A:
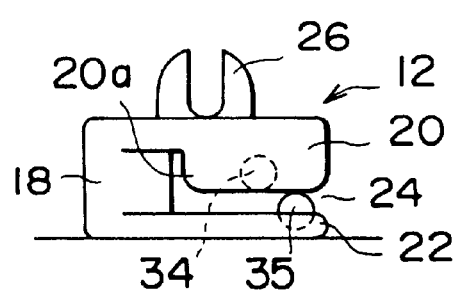
FIG. 4A is a right side view of another body to be screened in the body attitude screening apparatus of the embodiment of, the invention.
Figure 4B:
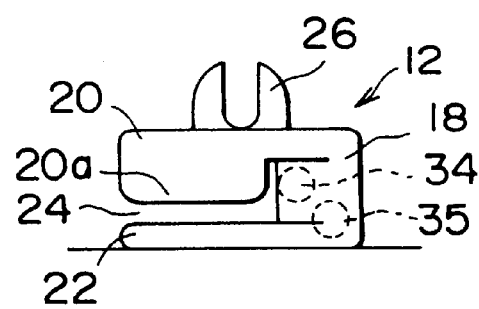
FIG. 4B is a left side view of another body to be screened in the body attitude screening apparatus of the embodiment of the invention.

With a body 12 in a different shape of a slide fastener slider, as shown in FIG. 4A, for example, structures of the upper plate 20, the lower plate 22, and the connecting post 18 are similar to those of the above embodiment, but at the side edge portions of the respective upper and lower plates 20 and 22, the guide flanges 20a standing perpendicularly toward the lower plate 22 are formed only on the upper plate 20. The guide flanges 20a are longer than those of the above embodiment and the lower plate 22 is formed into the flat plate without the guide flanges. Such a body 12 of the slide fastener slider is applied to a slide fastener chain wherein continuous coil-shaped fastener element rows are attached along opposed side edge portions of a pair of fastener tapes by sewing means such that the fastener element rows protrude on front sides of the fastener tapes. Assuming that the body 12 in the shape and attitude shown in FIG. 4A is the body 12 in a desired attitude and that the body 12 is traveling rightward in FIG. 4A, only the light emitted from the light emitting portion 35 of the attitude distinguishing sensor 30 passes through the tape groove 24 and reaches the light receiving portion 37, and the light emitted from the light emitting portion 34 of the attitude distinguishing sensor 30 is intercepted by the guide flange 20a of the upper plate 20 and does not reach the light receiving portion 36. On the other hand, in the case of a body 12 in an attitude as shown in FIG. 4B, because the lights from both the light emitting portions 34 and 35 of the attitude distinguishing sensor 30 are intercepted by the connecting post 18, the body 12 in the attitude shown in FIG. 4B is judged not to be in the desired attitude and sorted out and returned into the bowl as described above.

In the body attitude screening apparatus 10 of the slide fastener slider of the embodiment, by noting the shape of the body 12 of the slide fastener slider, the bodies 12 in different shapes as shown in FIGS. 3A, 3B, and 4A, 4B can be screened based on their attitudes by the same apparatus. Because the attitude screening of the bodies 12 is optically carried out by sensing presence/absence of the connecting post 18 of the body 12, it is unnecessary to adjust the presence/absence distinguishing sensor 28, the attitude distinguishing sensor 30, and the like of the body attitude screening apparatus 10, thereby dramatically improving sensing accuracy. Furthermore, because the two pairs of the light emitting and receiving portions of the attitude distinguishing sensor 30 are disposed diagonally with each other with respect to the traveling direction of the bodies 12, it is also possible to sense the attitude of the body 12 by light receiving timings of the light receiving portions 36 and 37, a large number of attitudes and shapes of the bodies 12 can be sensed, and various sensings are possible.

Because attitude screening is carried out by the optical sensors by utilizing characteristics of the body 12 of the slide fastener slider in the body attitude screening apparatus 10 of the slide fastener slider of the invention, it is unnecessary to provide body attitude screening apparatuses adapted to different shapes of the respective bodies, and the bodies in different shapes can be supplied accurately by the same body attitude screening apparatus. It is also possible to greatly shorten time required for change or adjustment to adapt the apparatus to the respective bodies in different shapes by using the same body attitude screening apparatus. Moreover, because varous bodies can be screened by the same body attitude screening apparatus, a number of lots in manufacturing the body attitude screening apparatuses can be increased, and thus, a manufacturing cost of the body attitude screening apparatus can be reduced. Also, it is unnecessary to develop various body attitude screening apparatuses, a low cost of development can be realized, and it is possible to manufacture products with high quality and at a low price.

What is claimed:

1. A body attitude screening apparatus for a slide fastener slider for transferring bodies along a transferring passage, sensing attitudes of said bodies, and supplying only said bodies in a desired attitude, each of said bodies having a flat upper and lower plates disposed in parallel to each other, a connecting post connecting said upper and lower plates, and a tape groove defined between said upper and lower plates, wherein said apparatus comprises a sensing portion which is provided at said transferring passage on which said bodies are transferred and which senses said attitudes of said bodies, and said sensing portion has a presence/absence distinguishing sensor for distinguishing presence and absence of each said body and an attitude distinguishing sensor for distinguishing said attitude of each said body in a direction orthogonal to a traveling direction of said body based on sensing of said presence/absence distinguishing sensor.

2. A body attitude screening apparatus for a slide fastener slider according to claim 1, wherein said attitude distinguishing sensor comprises two pairs of adjacent light emitting portions and light receiving portions and said attitude distinguishing sensor is disposed to distinguish said attitudes of said bodies based on two states, i.e., a state in which one of lights passing between said two pairs of light emitting portions and light receiving portions passes through said tape groove of each said body moving on said transferring passage and a state in which both said lights are intercepted by said connecting post of said body moving on said transferring passage.

3. A body attitude screening apparatus for a slide fastener slider according to claim 2, wherein said transferring passage has a transferring face inclined in a direction orthogonal to said traveling direction of said bodies and a guide portion connected to said transferring face along a lower end of said transferring face and projecting perpendicularly to said transferring face, any ones of said light emitting portions and said light receiving portions are disposed in said guide portion, and the others are disposed at a distance from said ones of said light emitting portions and said light receiving portions to face said ones of said light emitting portions and said light receiving portions.

4. A body attitude screening apparatus for a slide fastener slider according to claim 2, wherein said light emitting portions and said light receiving portions are disposed at diagonal positions displaced forward and backward from each other with respect to said traveling direction of said bodies.

5. A body attitude screening apparatus for a slide fastener slider according to claim 1, wherein said presence/absence distinguishing sensor has a light emitting portion and a light receiving portion disposed at positions on front and rear face sides of said transferring passage to face each other with said transferring passage disposed therebetween.

* * * * *